US00PP22109P2

(12) United States Plant Patent
Podaras

(10) Patent No.: US PP22,109 P2
(45) Date of Patent: Sep. 6, 2011

(54) ***BUDDLEJA* PLANT NAMED 'PODARAS #4'**

(50) Latin Name: *Buddleja weyeriana×Buddleja marubiafolia×(Buddleja davidii×Buddleja crispa)*
Varietal Denomination: Podaras #4

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,675

(22) Filed: Mar. 2, 2010

(51) Int. Cl.
*A01H 5/00* (2006.01)

(52) U.S. Cl. ..... Plt./242

(58) Field of Classification Search ..... Plt./242
See application file for complete search history.

*Primary Examiner* — Susan McCormick Ewoldt
(74) *Attorney, Agent, or Firm* — C. A. Whealy

(57) ABSTRACT

A new and distinct cultivar of *Buddleja* plant named 'Podaras #4', characterized by its upright and somewhat outwardly spreading plant habit; freely flowering habit; sterile light violet blue-colored flowers with yellow-colored centers; and good garden performance.

1 Drawing Sheet

Botanical designation: *Buddleja weyeriana×Buddleja marubiafolia×(Buddleja davidii×Buddleja crispa)*.

Cultivar denomination: 'PODARAS #4'.

BACKGROUND OF THE INVENTION

The present invention relates to a new and distinct cultivar of *Buddleja* plant, botanically known as *Buddleja weyeriana×Buddleja marubiafolia×(Buddleja davidii×Buddleja crispa)*and hereinafter referred to by the name 'Podaras #4'.

The new *Buddleja* plant is a product of a planned breeding program conducted by the Inventor in Ithaca, N.Y. The objective of the breeding program was to create new compact and sterile *Buddleja* plants with unique and attractive flower coloration.

The new *Buddleja* plant originated from a cross-pollination on Mar. 7, 2005 in Ithaca, N.Y., of *Buddleja weyeriana* 'Honeycomb', not patented, as the female, or seed, parent with an unnamed selection of *Buddleja marubiafolia×(Buddleja davidii×Buddleja crispa*, not patented, as the male, or pollen, parent. The new *Buddleja* plant was discovered and selected by the Inventor as a single flowering plant within the progeny of the stated cross-pollination in a controlled environment in Ithaca, N.Y. in September, 2007.

Asexual reproduction of the new *Buddleja* plant by cuttings in a controlled greenhouse environment in West Chicago, Ill. since February, 2008, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras #4'. These characteristics in combination distinguish 'Podaras #4' as a new and distinct *Buddleja* plant:

1. Upright and somewhat outwardly spreading plant habit.
2. Freely flowering habit.

3. Sterile light violet blue-colored flowers with yellow-colored centers.
4. Good garden performance.

Plants of the new *Buddleja* differ from plants of the female parent, 'Honeycomb', primarily in flower color as plants of 'Honeycomb' have yellow-colored flowers.

Plants of the new *Buddleja* differ from plants of the male parent selection primarily in flower color as plants of the male parent selection have pale purple-colored flowers.

Plants of the new *Buddleja* can be compared to plants of *Buddleja davidii* 'White Profusion', not patented. In side-by-side comparisons, plants of the new *Buddleja* and 'White Profusion' differed in the following characteristics:

1. Plants of the new *Buddleja* were more compact than plants of 'White Profusion'.
2. Plants of the new *Buddleja* and 'White Profusion' differed in flower color as plants of 'White Profusion' had white-colored flowers.
3. Flowers of plants of the new *Buddleja* were sterile whereas flowers of plants of 'White Profusion' were fertile.

BRIEF DESCRIPTION OF THE PHOTOGRAPHS

The accompanying colored photographs illustrate the overall appearance of the new *Buddleja* plant, showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Podaras #4' grown in a container.

The photograph at the top of the sheet is a close-up view of a typical inflorescence of 'Podaras #4'.

DETAILED BOTANICAL DESCRIPTION

The aforementioned photographs and following observations, measurements and values describe plants grown in Arroyo Grande, Calif. under commercial practice during the summer in 12.5-cm containers in a polyethylene-covered greenhouse with day temperatures averaging 21° C. and night temperatures averaging 7° C. Plants were pinched two times and were one year old when the photographs and description were taken. In the following description, color references are made to The Royal Horticultural Society Colour Chart, 2007 Edition, except where general terms of ordinary dictionary significance are used.

Botanical classification: *Buddleja weyeriana*×*Buddleja marubiafolia*×(*Buddleja davidii*×*Buddleja crispa*) 'Podaras #4'.

Parentage:

*Female, or seed, parent.*—*Buddleja weyeriana* 'Honeycomb', not patented.

*Male, or pollen, parent.*—Unnamed selection of *Buddleja marubiafolia*×(*Buddleja davidii*×*Buddleja crispa*), not patented.

Propagation:

*Type.*—By cuttings.

*Time to initiate roots plant, summer.*—About two weeks at temperatures of 18° C. to 24° C.

*Time to initiate roots plant, winter.*—About two weeks at temperatures of 18° C. to 24° C.

*Time to produce a rooted plant, summer.*—About 25 days at temperatures of 18° C. to 24° C.

*Time to produce a rooted plant, winter.*—About 30 days at temperatures of 18° C. to 24° C.

*Root description.*—Fibrous, fine; white in color.

*Rooting habit.*—Freely branching; moderately dense.

Plant description:

*Plant form/habit.*—Deciduous perennial shrub; upright and outwardly spreading plant habit; broad inverted triangle; vigorous growth habit.

*Plant height.*—About 78 cm.

*Plant width* (*spread*).—About 64 cm.

*Lateral branches.*—Quantity: About twelve main branches per plant. Length: About 74 cm. Diameter: About 6 mm. Internode length: About 5 cm. Strength: Strong. Texture, developing stems: Lanulose. Texture, mature stems: Smooth, glabrous. Color, developing: Close to 196A. Color, mature: Close to 199B.

Foliage description:

*Arrangement.*—Opposite, simple.

*Length.*—About 11.5 cm.

*Width.*—About 3.4 cm.

*Shape.*—Elliptical.

*Apex.*—Acute.

*Base.*—Attenuate.

*Margin.*—Serrulate.

*Texture, upper and lower surfaces.*—Pubescent.

*Venation pattern.*—Pinnate, reticulate.

*Color.*—Developing leaves, upper surface: Close to 191A. Developing leaves, lower surface: Close to 193C. Fully expanded leaves, upper surface: Close to 137A; venation, close to 194C. Fully expanded leaves, lower surface: Close to 196A; venation, close to 196A.

*Petiole.*—Length: About 6 mm. Diameter: About 2 mm. Texture, upper and lower surfaces: Lanulose. Color, upper and lower surfaces: Close to 194C.

Flower description:

*Flower type/habit.*—Single rotate and salverform flowers arranged in compound terminal and axillary panicles; flowers face upright and outward; panicles roughly conical in shape; freely flowering habit with about 620 flower buds and flowers developing per inflorescence.

*Fragrance.*—Faint, sweet.

*Natural flowering season.*—Plants begin flowering about three months after planting; flowering continuous from spring until frost in California.

*Postproduction longevity.*—Flowers last about three to four days on the plant; flowers persistent.

*Flower buds.*—Height: About 1.2 cm. Diameter: About 3 mm. Shape: Oblong. Color: Close to 97B.

*Inflorescence height.*—About 21 cm.

*Inflorescence diameter.*—About 7 cm.

*Flower diameter.*—About 1 cm.

*Flower depth.*—About 1.4 cm.

*Flower throat, diameter.*—About 2 mm.

*Flower tube, length.*—About 1.1 cm.

*Flower tube, diameter at base.*—About 1.5 mm.

*Petals.*—Quantity per flower: Typically four in a single whorl; petals fused into a narrow tube. Lobe length: About 4 mm. Lobe width: About 4 mm. Lobe shape: Roughly spatulate. Lobe apex: Rounded. Lobe margin: Minutely erose, crinkled. Texture, upper and lower lobe surfaces: Smooth, glabrous. Texture, throat: Slightly pubescent. Texture, tube: Slightly pubescent. Color: Developing petals, upper surface: Close to 100D; towards the throat, close to 8C. Developing petals, lower surface: Close to 97B. Fully expanded petals, upper surface: Close to 97C; towards the throat, close to 8A to 8B; venation, close to 8A to 8B; color becoming closer to 8A to 8C with development. Fully expanded petals, lower surface: Close to 1D; venation, close to 1D. Throat: Close to N163A; venation, close to N163A. Tube: Close to 173C; venation, close to 173C.

*Sepals.*—Quantity per flower: Typically four in a single whorl, fused towards the base; campanulate calyx. Length: About 3 mm. Width: About 1 mm. Shape: Lanceolate. Apex: Acute. Margin: Entire. Texture, upper surface: Smooth, glabrous. Texture, lower surface: Pubescent. Color, upper surface: Close to 145A. Color, lower surface: Close to 195C.

*Peduncles.*—Length: About 3.5 cm. Diameter: About 3 mm. Angle: Erect to about 45° from vertical. Strength: Strong. Texture: Pubescent. Color: Close to 195B.

*Pedicels.*—Length: About 4 mm. Diameter: About 1.5 mm. Angle: About 45° from peduncle axis. Strength: Strong. Texture: Lanulose. Color: Close to 195B.

*Reproductive organs.*—Stamens: Quantity per flower: Typically four; filaments adnate to the corolla tube. Filament length: About 1.5 mm. Filament color: Close to N163A. Anther shape: Lanceolate. Anther length: About 1 mm. Anther color: Close to 156D. Pollen amount: None. Pistils: Quantity per flower: One. Pistil length: About 4 mm. Stigma shape: Oval. Stigma color: Close to N144B. Style length: About 1 mm. Style color: Close to 145C. Ovary color: Close to 193A.

*Seed/fruit.*—Flowers of plants of the new *Buddleja* are sterile and seed and fruit development have not been observed.

Disease/pest resistance: Plants of the new *Buddleja* have been not been observed to be resistant to pathogens and pests common to *Buddleja*.

Garden performance: Plants of the new *Buddleja* have been observed to have good garden performance and tolerate rain, wind and temperatures ranging from about 0° C. to about 40° C.

It is claimed:

1. A new and distinct *Buddleja* plant named 'Podaras #4' as illustrated and described.

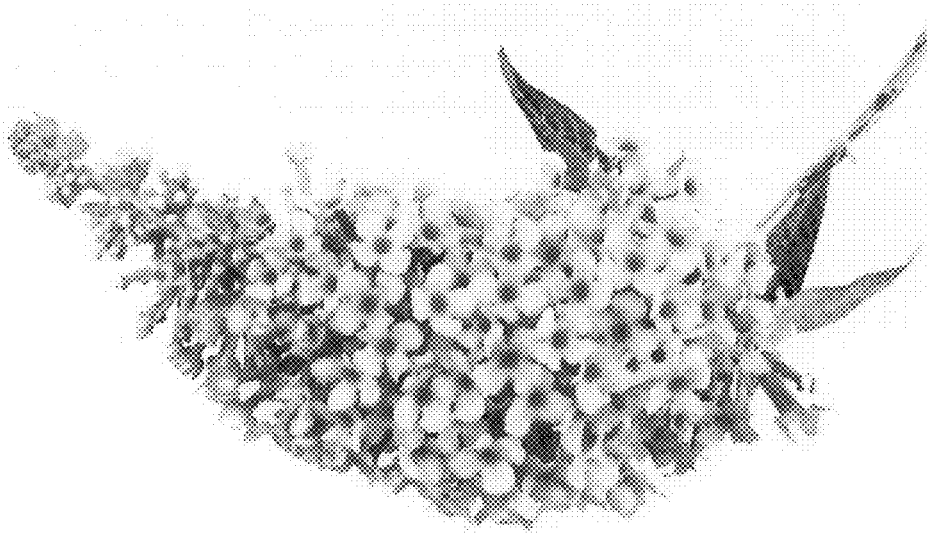
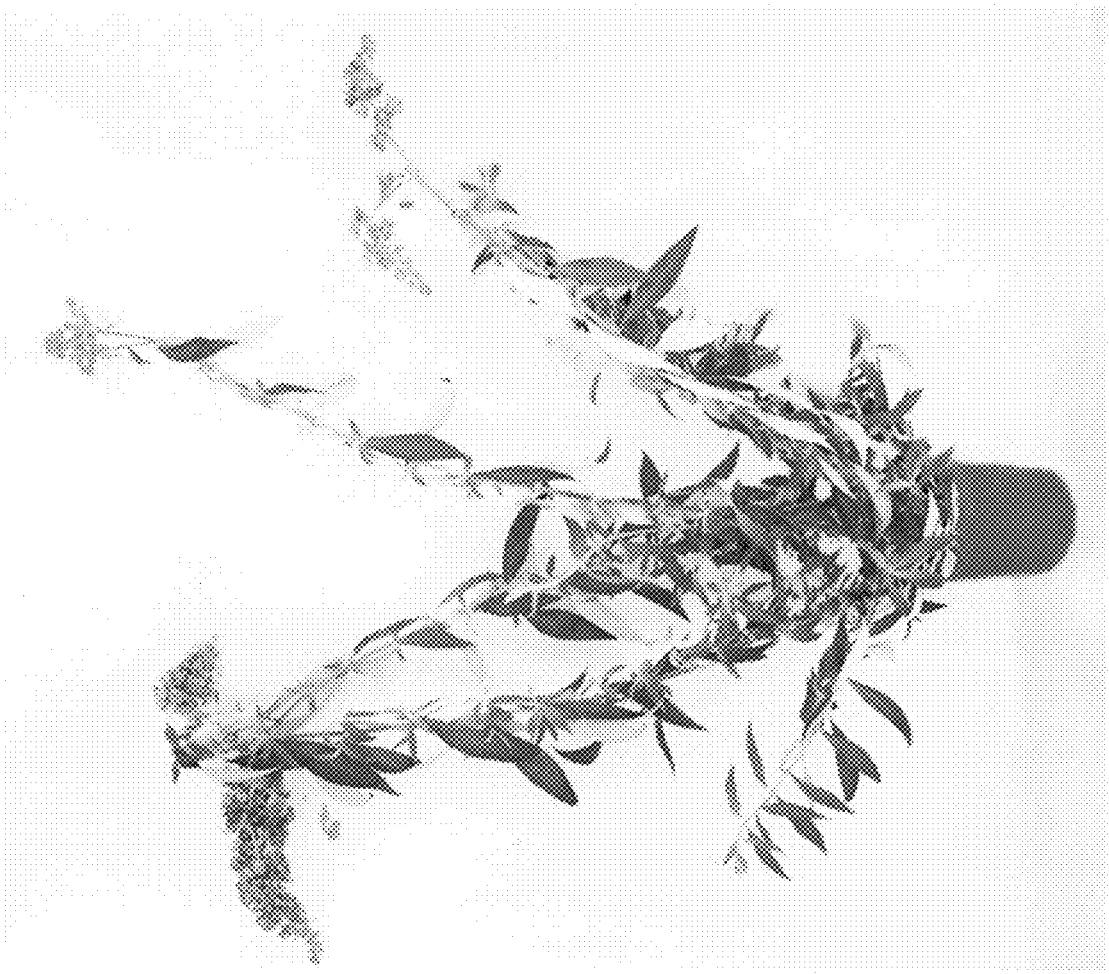

* * * * *